United States Patent
Wu

(10) Patent No.: US 8,854,616 B2
(45) Date of Patent: Oct. 7, 2014

(54) VISUAL INSPECTION APPARATUS FOR GLASS SUBSTRATE OF LIQUID CRYSTAL DISPLAY AND INSPECTION METHOD THEREOF

(75) Inventor: Jo-Shan Wu, Shenzhen (CN)

(73) Assignee: Shenzhen China Star Optoelectronics Technology Co., Ltd., Shenzhen (CN)

( * ) Notice: Subject to any disclaimer, the term of this patent is extended or adjusted under 35 U.S.C. 154(b) by 502 days.

(21) Appl. No.: 13/378,670

(22) PCT Filed: Sep. 5, 2011

(86) PCT No.: PCT/CN2011/079341
§ 371 (c)(1),
(2), (4) Date: Dec. 15, 2011

(87) PCT Pub. No.: WO2013/016889
PCT Pub. Date: Feb. 7, 2013

(65) Prior Publication Data
US 2013/0033706 A1    Feb. 7, 2013

(30) Foreign Application Priority Data
Aug. 3, 2011  (CN) .......................... 2011 1 0220835

(51) Int. Cl.
*G01N 21/00* (2006.01)
*G01N 21/95* (2006.01)
*G01N 21/958* (2006.01)

(52) U.S. Cl.
CPC ........ *G01N 21/95* (2013.01); *G01N 2021/9513* (2013.01); *G01N 21/958* (2013.01)
USPC .................. 356/239.1; 356/239.7; 356/237.2; 356/237.4

(58) Field of Classification Search
None
See application file for complete search history.

(56) References Cited

U.S. PATENT DOCUMENTS

| | | | | |
|---|---|---|---|---|
| 3,772,949 A | * | 11/1973 | Pavone et al. ...................... 83/56 |
| 4,171,657 A | * | 10/1979 | Halberschmidt et al. ....... 83/886 |
| 4,386,470 A | * | 6/1983 | Perry ............................... 33/438 |
| 4,738,029 A | * | 4/1988 | Held .............................. 33/18.1 |
| 4,995,277 A | * | 2/1991 | Yanagisawa ............... 74/490.09 |
| 5,287,629 A | * | 2/1994 | Pettersson ....................... 33/503 |
| 5,309,108 A | * | 5/1994 | Maeda et al. .................. 324/501 |

(Continued)

FOREIGN PATENT DOCUMENTS

CN   2114804 U   9/1992
CN   2470821 Y   1/2002

(Continued)

*Primary Examiner* — Tarifur Chowdhury
*Assistant Examiner* — Jarreas C Underwood
(74) *Attorney, Agent, or Firm* — Mark M. Friedman

(57) ABSTRACT

Disclosed is a visual inspection apparatus for a glass substrate of a liquid crystal display, comprising an inspection platform and at least two slide rails. The glass substrate for inspection is fixedly located on an inspection platform main body. The slide rails are installed at two adjacent sides of the main body leastwise. Length directions of the slide rails are parallel with a level of the main body. The lengths of the two adjacent slide rails are mutually perpendicular; the visual inspection apparatus further comprises a coordinate reader. The coordinate reader is slidably jointed to the slide rails and employed to cross above the level of the main body to form a locating point. An inspector reads a coordinate of the locating point to acquire a corresponding coordinate of the glass substrate. The present invention also provides an inspection method for a glass substrate of a liquid crystal display.

12 Claims, 4 Drawing Sheets

(56) References Cited

U.S. PATENT DOCUMENTS

| | | | |
|---|---|---|---|
| 5,650,852 A * | 7/1997 | Chastain et al. | 356/630 |
| 5,661,559 A * | 8/1997 | Brezoczky et al. | 356/512 |
| 6,058,618 A * | 5/2000 | Hemmelgarn et al. | 33/503 |
| 6,163,973 A * | 12/2000 | Matsumiya et al. | 33/559 |
| 6,430,828 B1 * | 8/2002 | Ulbrich | 33/503 |
| 6,442,857 B1 * | 9/2002 | Atsuhiko et al. | 33/553 |
| 6,556,783 B1 * | 4/2003 | Gelphman | 396/20 |
| 6,647,632 B2 * | 11/2003 | Tominaga et al. | 33/1 M |
| 7,017,896 B2 * | 3/2006 | Sa | 269/55 |
| 7,095,534 B2 * | 8/2006 | Hayashi | 358/474 |
| 7,307,444 B2 * | 12/2007 | Umetsu et al. | 356/432 |
| 7,675,625 B2 * | 3/2010 | Yoon | 356/445 |
| 7,684,057 B2 * | 3/2010 | Sakai | 356/614 |
| 7,751,609 B1 * | 7/2010 | Berman | 382/141 |
| 2004/0207836 A1 * | 10/2004 | Chhibber et al. | 356/237.4 |
| 2004/0231177 A1 | 11/2004 | Mies | |
| 2005/0099204 A1 * | 5/2005 | Uh et al. | 324/770 |

FOREIGN PATENT DOCUMENTS

| | | |
|---|---|---|
| CN | 1442688 A | 9/2003 |
| CN | 1464969 A | 12/2003 |
| CN | 1532521 A | 9/2004 |
| CN | 1532534 A | 9/2004 |
| CN | 1566971 A | 1/2005 |
| CN | 1808055 A | 7/2006 |
| CN | 201014999 Y | 1/2008 |
| CN | 201311924 Y | 9/2009 |
| CN | 201555577 U | 8/2010 |
| FR | 2625707 A1 | 7/1989 |
| GB | 2354864 A | 4/2001 |

* cited by examiner

VISUAL INSPECTION APPARATUS FOR GLASS SUBSTRATE OF LIQUID CRYSTAL DISPLAY AND INSPECTION METHOD THEREOF

BACKGROUND OF THE INVENTION

1. Field of the Invention

The present invention generally relates to a LCD manufacture technology field, and more particularly to a visual inspection apparatus for a glass substrate of a liquid crystal display and an inspection method for the glass substrate of the liquid crystal display.

2. Description of Prior Art

With the unceasing development of the LCD technology, seriously high demand advances for the manufacture of the liquid crystal display.

Taking the thin film transistor (TFT)_display as an example, a large size glass substrate is now widely available as the size of the TFT display is getting larger and larger.

In the inspection platform according to prior art, an inspector generally acquires the coordinates of the glass substrate with visual measurement.

Please refer to FIG. 1, which shows a structure diagram of a visual inspection apparatus according to prior art. The visual inspection apparatus comprises an inspection platform 100. The inspection platform 100 comprises an inspection platform main body 101. The glass substrate for inspection is fixedly located on the inspection platform main body 101. The visual inspection apparatus further comprises two graduators 102. The graduators 102 are mutually perpendicular and installed at two sides of the inspection platform main body 101. After the glass substrate for inspection is located on the inspection platform main body 101, the inspector reads a coordinate of a certain point via the graduators 102 by visual measurement.

The inspection procedure for a glass substrate of a liquid crystal display has drawbacks described below:
1. Different inspectors may acquire different read results.
2. An enormous inaccuracy between the actual red coordinate and the real coordinate may happen and the maximal error may up to 50 mm because the coordinate of the glass substrate for inspection cannot be accurate.
3. Because the red coordinate of the glass substrate is inaccurate, wrong inspection information may easily appear. Only photorefraction can be utilized for measurement once special inspection with an oblique angle becomes necessary. The resolution efficiency of the abnormal issues is concerned.
4. Because the magnification of the present inspection apparatus is large and the field of vision diminishes. Generally, the maximal field of vision may up to 5 mm and results in that a blind area exists for the inaccurate inspection. Please refer to FIG. 2, which shows a sectional structure diagram of a visual inspection apparatus according to prior art. The location indicated by the alphabet a in FIG. 2 is a notching area at the edge of the visual inspection apparatus, i.e. the blind area.

In conclusion, as the inspection is proceeded to the glass substrate, due to the factors of the size of the glass substrate, the inspection distance and the inspection angle, it is difficult to accurately read the corresponding coordinate. Besides, the wrong inspection result occurs due to the blind area existence.

SUMMARY OF THE INVENTION

An objective of the present invention is to provide a visual inspection apparatus for a glass substrate of a liquid crystal display to solve problems of reading the corresponding coordinate inaccurately and the wrong inspection result due to the blind area existence.

For solving the aforesaid problems, the present invention provides a visual inspection apparatus for a glass substrate of a liquid crystal display, comprising an inspection platform, and the inspection platform comprises an inspection platform main body which the glass substrate for inspection is fixedly located thereon, the visual inspection apparatus further comprises a first slide rail and a third slide rail, and the first slide rail and the third slide rail are installed at two adjacent sides of the inspection platform main body, and length directions of the slide rails are parallel with a level of the inspection platform main body, and the length directions of the first slide rail and the third slide rail are mutually perpendicular;

the visual inspection apparatus further comprises a coordinate reader, and the coordinate reader comprises a first movable ruler and a second movable ruler, and the first movable ruler and the second movable ruler are respectively slidably jointed to the first slide rail and the third slide rail, and the first movable ruler and the second movable ruler are employed to cross above the level of the inspection platform main body to form a locating point, and an inspector reads an coordinate of the locating point to acquire a corresponding coordinate of the glass substrate for inspection;

wherein a length direction of the first movable ruler is perpendicular to a length direction of the first slide rail; a length direction of second movable ruler is perpendicular to a length direction of the third slide rail;

the coordinate reader further comprises a first ruler and a second ruler; wherein a length direction of the first ruler is parallel with the length direction of the first slide rail; a length direction of the second ruler is parallel with the length direction of the third slide rail.

In the visual inspection apparatus for a glass substrate of a liquid crystal display according to the present invention, the slide rails further comprises a second slide rail and fourth slide rail, wherein a length direction of second slide rail is parallel with the length direction of the first slide rail, and the first slide rail and the second slide rail are positioned at two opposite sides of the inspection platform main body, and the first movable ruler is slidably jointed to the first slide rail and the second slide rail;

a length direction of fourth slide rail is parallel with the length direction of the third slide rail, and the third slide rail and the fourth slide rail are positioned at two opposite sides of the inspection platform main body, and the second movable ruler is slidably jointed to the third slide rail and the fourth slide rail.

In the visual inspection apparatus for a glass substrate of a liquid crystal display according to the present invention, the coordinate reader further comprises a first pointer and a second pointer;

wherein the first pointer is slidably jointed to the first slide rail, and the first ruler is positioned corresponding to the first pointer;

the second pointer is slidably jointed to the second slide rail, and the second ruler is positioned corresponding to the second pointer.

In the visual inspection apparatus for a glass substrate of a liquid crystal display according to the present invention, the first pointer and the second pointer are laser pens.

Another objective of the present invention is to provide an inspection method for a glass substrate of a liquid crystal display to solve problems of reading the corresponding coordinate inaccurately and the wrong inspection result due to the blind area existence.

For solving the aforesaid problems, the present invention provides an inspection method for a glass substrate of a liquid crystal display comprising steps of:
locating the glass substrate for inspection fixedly on an inspection platform main body;
acquiring a corresponding coordinate via a coordinate reader installed on slide rails;
comparing the acquired coordinate with an inspection standard of the glass substrate to determine whether the glass substrate coincides the inspection standard;
wherein the slide rails are installed at two adjacent sides of the inspection platform main body leastwise, and length directions of the slide rails are parallel with a level of the inspection platform main body, and the lengths of the two adjacent slide rails are mutually perpendicular; the coordinate reader is slidably jointed to the slide rails.

In the inspection method for a glass substrate of a liquid crystal display, the step of acquiring a corresponding coordinate via the coordinate reader installed on the slide rails further comprises steps of:
controlling a first movable ruler sliding along a first slide rail;
controlling a second movable ruler sliding along a third slide rail;
acquiring the corresponding coordinate according to the first movable ruler and the second movable ruler;
wherein a length direction of the first movable ruler is perpendicular to a length direction of the first slide rail; a length direction of second movable ruler is perpendicular to a length direction of the third slide rail.

In the inspection method for a glass substrate of a liquid crystal display, the step of acquiring a corresponding coordinate via the coordinate reader installed on the slide rails further comprises steps of:
controlling the first movable ruler sliding along the first slide rail and a second slide rail;
controlling the second movable ruler sliding along the third slide rail and a fourth slide rail;
acquiring the corresponding coordinate according to the first movable ruler and the second movable ruler;
wherein a length direction of second slide rail is parallel with the length direction of the first slide rail, and the first slide rail and the second slide rail are positioned at two opposite sides of the inspection platform main body; a length direction of fourth slide rail is parallel with the length direction of the third slide rail, and the third slide rail and the fourth slide rail are positioned at two opposite sides of the inspection platform main body.

In the inspection method for a glass substrate of a liquid crystal display, the step of acquiring a corresponding coordinate via the coordinate reader installed on the slide rails further comprises steps of:
controlling a first pointer sliding along a fifth slide rail;
controlling a second pointer sliding along a sixth slide rail;
acquiring the corresponding coordinate according to an optical line of the first pointer corresponding to the graduations of the first ruler and an optical line of the second pointer corresponding to the graduations of the second ruler;
wherein a length direction of the first ruler is parallel with a length direction of the fifth slide rail and corresponds to the first pointer; a length direction of the second ruler is parallel with a length direction of the sixth slide rail and corresponds to the second pointer.

In the inspection method for a glass substrate of a liquid crystal display, the first pointer and the second pointer are laser pens.

Comparing with prior art, the present invention eliminates the technical problems of inaccurately reading the corresponding coordinate and the wrong inspection result due to the blind area existence efficiently to promote the inspection accuracy of the glass substrate.

For a better understanding of the aforementioned content of the present invention, preferable embodiments are illustrated in accordance with the attached figures for further explanation:

DETAILED DESCRIPTION OF THE INVENTION

The following descriptions for the respective embodiments are specific embodiments capable of being implemented for illustrations of the present invention with referring to appended figures.

Figure 3:
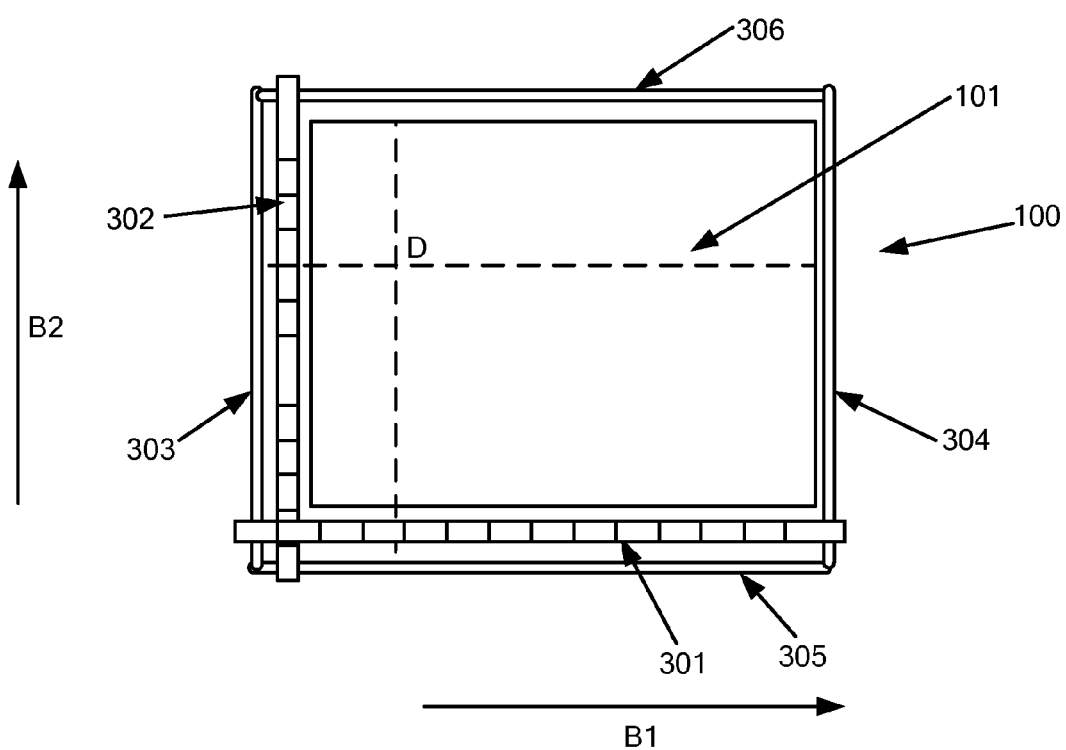
FIG. 3 shows a structure diagram of a visual inspection apparatus for a glass substrate of a liquid crystal display according to a first preferable embodiment of the present invention.

Please refer to FIG. 3, which shows a structure diagram of a visual inspection apparatus for a glass substrate of a liquid crystal display according to a first preferable embodiment of the present invention.

In the first preferable embodiment shown in FIG. 3, the visual inspection apparatus comprises an inspection platform 100. The inspection platform 100 comprises an inspection platform main body 101.

Please refer to FIG. 3, the visual inspection apparatus further comprises slide rails and a coordinate reader (now shown). The coordinate reader comprises a movable ruler 301 extending along a transverse direction B1 and a movable ruler 302 extending along a straight direction B2. Correspondingly, the slides further comprises a slide rail 303 and a slide rail 304 extending along a straight direction B2 and a slide rail 305 and a slide rail 306 extending along a transverse direction B1.

The movable ruler 301 is slidably jointed to the slide rail 303 and the slide rail 304. The movable ruler 302 is slidably jointed to the slide rail 305 and the slide rail 306.

In the specific embodiment, the movable ruler 301 can be slidably jointed to the slide rail 303 only and the movable ruler 302 can be slidably jointed to the slide rail 305 only. Similar principle of operation is applied and description is omitted here.

In the first preferable embodiment shown in FIG. 3, a length direction of the movable ruler 301 is perpendicular to length directions of the slide rail 303 and the slide rail 304; the movable ruler 302 is perpendicular to length directions of the slide rail 305 and the slide rail 306. All the length directions of the slide rails 303, 304 and the length directions of the slide rails 305, 306 are parallel with a level of the inspection platform main body 101.

In the first preferable embodiment shown in FIG. 3, after the glass substrate for inspection is located on the inspection platform main body 101, the movable ruler 301 is controlled to slide along the slide rail 303 and the slide rail 304, i.e. the straight direction B2. Meanwhile, the movable ruler 302 is controlled to slide along the slide rail 305 and the slide rail 306, i.e. the transverse direction B1. After the movable ruler 301 and the movable ruler 302 are slid to stop at certain positions, the movable ruler 301 and the movable ruler 302 cross above the level of the inspection platform main body 101 to form a locating point D. The inspector reads a coordinate of the locating point D via the graduations of the movable ruler 301 and the graduations of the movable ruler 302. The coordinate of the locating point D represents the corresponding coordinate located on the glass substrate for inspection. Apparently, the embodiment realizes an accurate location for the glass substrate of the liquid crystal display for inspection.

Figure 1:
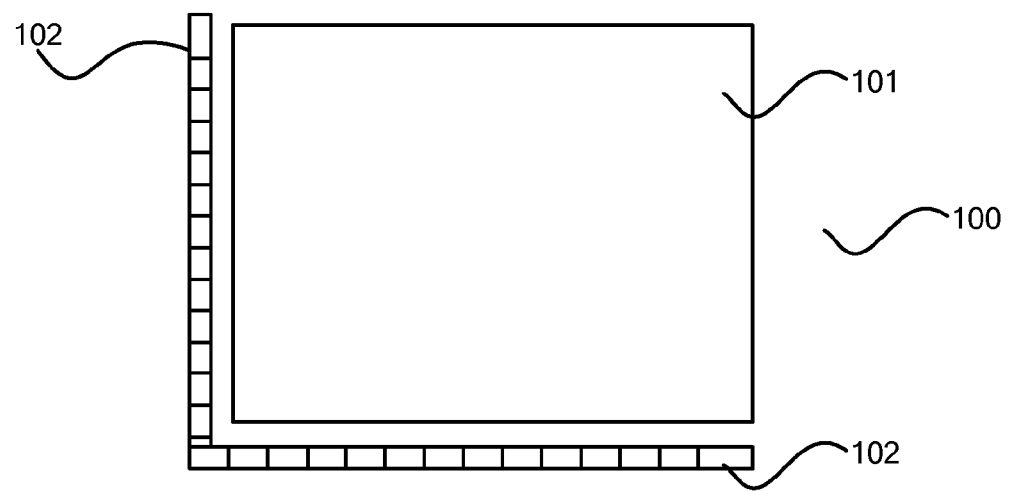
FIG. 1 shows a structure diagram of a visual inspection apparatus according to prior art.
Figure 2:
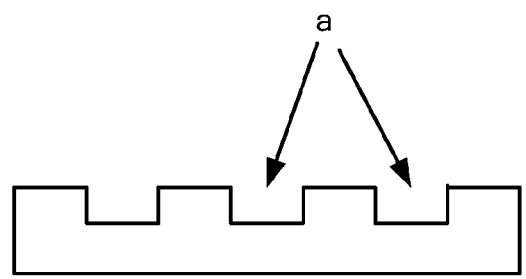
FIG. 2 shows a sectional structure diagram of a visual inspection apparatus according to prior art.

Moreover, in the first preferable embodiment shown in FIG. 3, because the slide rails are close to the inspection platform main body 101, and installed at two adjacent sides of the inspection platform main body, the coordinate of any location on the glass substrate for inspection on the inspection platform main body 101 can be acquired to prevent the wrong inspection due to the existing blind area in FIG. 2. The accuracy of read result can be guaranteed.

Figure 4:
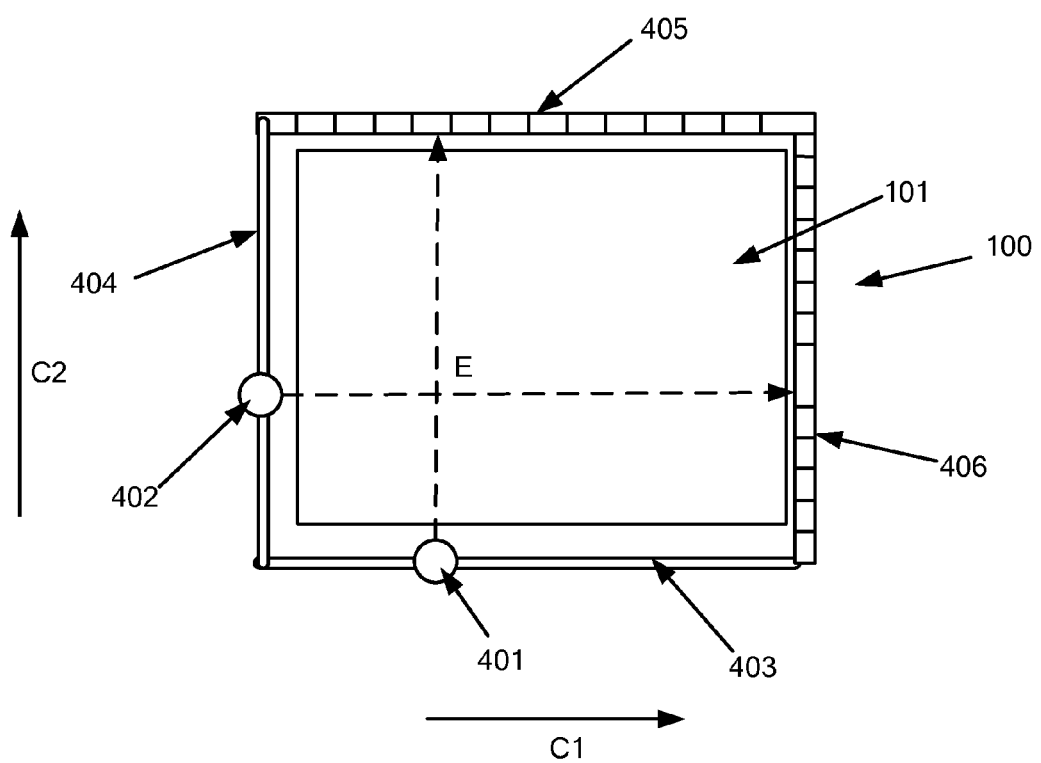
FIG. 4 shows a structure diagram of a visual inspection apparatus for a glass substrate of a liquid crystal display according to a second preferable embodiment of the present invention.

Please refer to FIG. 4. FIG. 4 shows a structure diagram of a visual inspection apparatus for a glass substrate of a liquid crystal display according to a second preferable embodiment of the present invention.

In the second preferable embodiment shown in FIG. 4, the visual inspection apparatus comprises an inspection platform 100. The inspection platform 100 comprises an inspection platform main body 101.

In comparison with the first preferable embodiment shown in FIG. 3, the slide rails comprises a slide rail 403 extending along the transverse direction C1 and a slide rail 404 extending along the straight direction C2 in the second preferable embodiment in shown in FIG. 4. The coordinate reader comprises a pointer 401, a pointer 402, a ruler 405 and a ruler 406.

Please refer to FIG. 4. The pointer 401 is slidably jointed to the slide rail 403 and corresponds to the ruler 405; the pointer 402 is slidably jointed to the slide rail 404 and corresponds to the ruler 406.

In the second preferable embodiment in shown in FIG. 4, a length direction of the ruler 405 is parallel with the length direction of the slide rail 403; a length direction of the ruler 406 is parallel with the length direction of the slide rail 404. Both the length directions of the slide rail 403 and the slide rail 404 are parallel with a level of the inspection platform main body 101.

In the second preferable embodiment in shown in FIG. 4, after the glass substrate for inspection is located on the inspection platform main body 101, the pointer 401 is controlled to slide along the slide rail 403, i.e. the transverse direction C1. Meanwhile, the pointer 402 is controlled to slide along the slide rail, i.e. the transverse direction C2. After the pointer 401 and the pointer 402 are slid to stop at certain positions, the optical lines of the pointer 401 and the pointer 402 cross to form a locating point E. The inspector reads a coordinate of the locating point E via the graduations of the ruler 405 that the optical line of the pointer 401 points at and the graduations of the ruler 406 that the optical line of the pointer 402 points at. The coordinate of the locating point E represents the corresponding coordinate on the glass substrate for inspection. Apparently, the embodiment realizes an accurate location for the glass substrate of the liquid crystal display for inspection.

Moreover, in the first preferable embodiment shown in FIG. 4, the slide rails and rulers are close to the inspection platform main body 101. The slide rails are installed at two adjacent sides of the inspection platform main body and the rulers are positioned at the other two sides corresponding to the slide rails. Therefore, the coordinate of any location on the glass substrate for inspection on the inspection platform main body 101 can be acquired to prevent the wrong inspection due to the existing blind area in FIG. 2.

Figure 5:
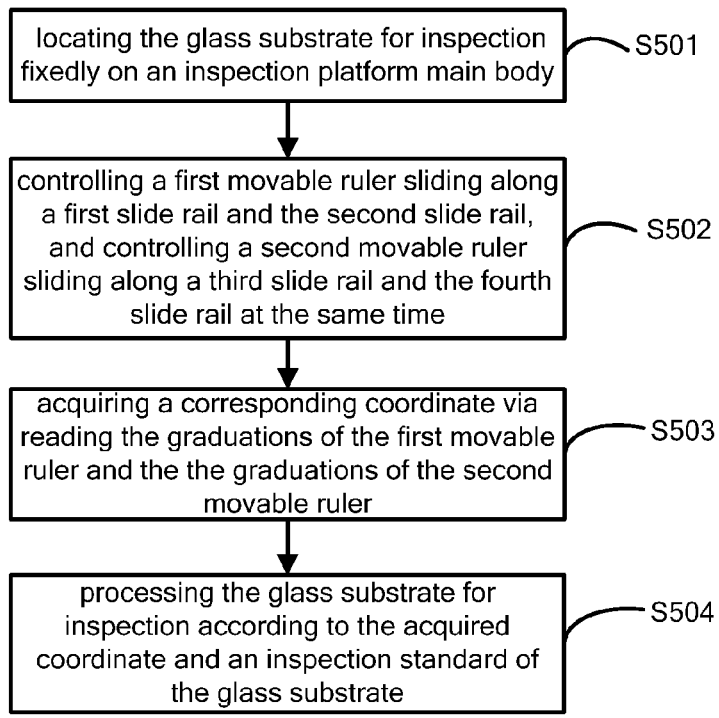
FIG. 5 shows a flow chart of an inspection method for a glass substrate of a liquid crystal display according to a first preferable embodiment of the present invention.

Please refer to FIG. 5. FIG. 5 shows a flow chart of an inspection method for a glass substrate of a liquid crystal display according to a first preferable embodiment of the present invention.

In Step 501, locating the glass substrate for inspection fixedly on an inspection platform main body 101.

In Step 502, controlling a first movable ruler sliding along a first slide rail and the second slide rail, and controlling a second movable ruler sliding along a third slide rail and the fourth slide rail at the same time.

In the specific embodiment, the first movable ruler can be slidably jointed to the first slide rail only and the second movable ruler can be slidably jointed to the third slide rail only. Similar principle of operation is applied and description is omitted here.

A length direction of the first movable ruler is perpendicular to a length direction of the first slide rail; a length direction of second movable ruler is perpendicular to a length direction of the third slide rail.

A length direction of second slide rail is parallel with the length direction of the first slide rail, and the first slide rail and the second slide rail are positioned at two opposite sides of the inspection platform main body; a length direction of fourth slide rail is parallel with the length direction of the third slide rail, and the third slide rail and the fourth slide rail are positioned at two opposite sides of the inspection platform main body.

In Step 503, acquiring a corresponding coordinate via reading the graduations of the first movable ruler and the graduations of the second movable ruler after the first movable ruler and the second movable ruler are slid to stop at certain positions.

In Step 504, processing the glass substrate for inspection according to the acquired coordinate and an inspection standard of the glass substrate.

The inspection standard is a cutting standard for the glass substrate or the size specification provided by the maker. The related detail description is omitted here.

In the embodiment of the present invention, the inspector can read the coordinate of any location on the glass substrate accurately via the coordinate reader after the glass substrate for inspection is located on the inspection platform main body. The problems of the low accuracy caused by acquiring the coordinates by estimation in prior art.

Figure 6:
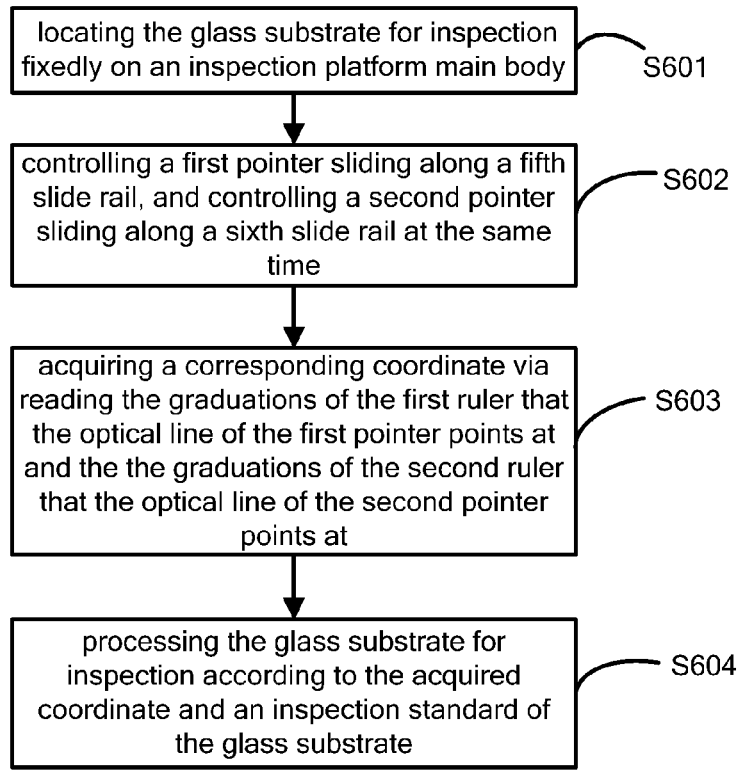
FIG. 6 shows a flow chart of an inspection method for a glass substrate of a liquid crystal display according to a second preferable embodiment of the present invention.

FIG. 6 shows a flow chart of an inspection method for a glass substrate of a liquid crystal display according to a second preferable embodiment of the present invention.

In Step 601, locating the glass substrate for inspection fixedly on an inspection platform main body 101.

In Step 602, controlling a first pointer sliding along a fifth slide rail, and controlling a second pointer sliding along a sixth slide rail at the same time.

In Step 603, acquiring a corresponding coordinate via reading the graduations of the first ruler that the optical line of the first pointer points at and the the graduations of the second ruler that the optical line of the second pointer points at after the first pointer and the second pointer are slid to stop at certain positions.

In Step 604, processing the glass substrate for inspection according to the acquired coordinate and an inspection standard of the glass substrate.

A length direction of the first ruler is parallel with a length direction of the fifth slide rail and corresponds to the first pointer; a length direction of the second ruler is parallel with a length direction of the sixth slide rail and corresponds to the second pointer.

Preferably, the first pointer and the second pointer are laser pens. Other instruments which can generate optical line also can be illustrated as being the pointers. The detail description is omitted here.

As is understood by a person skilled in the art, the foregoing preferred embodiments of the present invention are illustrative rather than limiting of the present invention. It is intended that they cover various modifications and similar arrangements be included within the spirit and scope of the appended claims, the scope of which should be accorded the broadest interpretation so as to encompass all such modifications and similar structure.

What is claimed is:

1. A visual inspection apparatus for a glass substrate of a liquid crystal display, comprising an inspection platform, and the inspection platform comprises an inspection platform main body which the glass substrate for inspection is fixedly located thereon, characterized in that, the visual inspection apparatus further comprises a first slide rail and a third slide rail, and the first slide rail and the third slide rail are installed at two adjacent sides of the inspection platform main body, and length directions of the slide rails are parallel with a level of the inspection platform main body, and the length directions of the first slide rail and the third slide rail are mutually perpendicular;

the visual inspection apparatus further comprises a coordinate reader, and the coordinate reader comprises a first movable ruler and a second movable ruler, and the first movable ruler and the second movable ruler are respectively slidably jointed to the first slide rail and the third slide rail, and the first movable ruler and the second movable ruler are employed to cross above the level of the inspection platform main body to form a locating point, and an inspector reads an coordinate of the locating point to acquire a corresponding coordinate of the glass substrate for inspection;

wherein a length direction of the first movable ruler is perpendicular to a length direction of the first slide rail; a length direction of second movable ruler is perpendicular to a length direction of the third slide rail;

the coordinate reader further comprises a first ruler and a second ruler; wherein a length direction of the first ruler is parallel with the length direction of the first slide rail; a length direction of the second ruler is parallel with the length direction of the third slide rail.

2. The visual inspection apparatus for a glass substrate of a liquid crystal display according to claim 1, characterized in that the slide rails further comprises a second slide rail and fourth slide rail, wherein a length direction of second slide rail is parallel with the length direction of the first slide rail, and the first slide rail and the second slide rail are positioned at two opposite sides of the inspection platform main body, and the first movable ruler is slidably jointed to the first slide rail and the second slide rail;

a length direction of fourth slide rail is parallel with the length direction of the third slide rail, and the third slide rail and the fourth slide rail are positioned at two opposite sides of the inspection platform main body, and the second movable ruler is slidably jointed to the third slide rail and the fourth slide rail.

3. The visual inspection apparatus for a glass substrate of a liquid crystal display according to claim 1, characterized in that the coordinate reader further comprises a first pointer and a second pointer;

wherein the first pointer is slidably jointed to the first slide rail, and the first ruler is positioned corresponding to the first pointer;

the second pointer is slidably jointed to the second slide rail, and the second ruler is positioned corresponding to the second pointer.

4. The visual inspection apparatus for a glass substrate of a liquid crystal display according to claim 1, characterized in that the first pointer and the second pointer are laser pens.

5. A visual inspection apparatus for a glass substrate of a liquid crystal display, comprising an inspection platform, and the inspection platform comprises an inspection platform main body which the glass substrate for inspection is fixedly located thereon, characterized in that, the visual inspection apparatus further comprises at least two slide rails, and the slide rails are installed at two adjacent sides of the inspection platform main body leastwise, and length directions of the slide rails are parallel with a level of the inspection platform main body, and the lengths of the two adjacent slide rails are mutually perpendicular;

the visual inspection apparatus further comprises a coordinate reader, and the coordinate reader is slidably jointed to the slide rails, and the coordinate reader is employed to cross above the level of the inspection platform main body to form a locating point, and an inspector reads an coordinate of the locating point to acquire a corresponding coordinate of the glass substrate for inspection, wherein the slide rails further comprises a fifth slide rail and sixth slide rail; the coordinate reader further comprises a first pointer, a second pointer, a first ruler and a second ruler;

wherein the first pointer is slidably jointed to the fifth slide rail, and the first ruler is positioned corresponding to the first pointer, and a length direction of the first ruler is parallel with a length direction of the fifth slide rail;

the second pointer is slidably jointed to the sixth slide rail, and the second ruler is positioned corresponding to the second pointer, and a length direction of the second ruler is parallel with a length direction of the sixth slide rail.

6. The visual inspection apparatus for a glass substrate of a liquid crystal display according to claim 5, characterized in that the slide rails further comprises a first slide rail and a third slide rail; the coordinate reader further comprises a first movable ruler and a second movable ruler, the first movable ruler is slidably jointed to the first slide rail, and a length direction of the first movable ruler is perpendicular to a length direction of the first slide rail;

the second movable ruler is slidably jointed to the third slide rail, and a length direction of second movable ruler is perpendicular to a length direction of the third slide rail.

7. The visual inspection apparatus for a glass substrate of a liquid crystal display according to claim 6, characterized in that the slide rails further comprises a second slide rail and fourth slide rail,
wherein a length direction of second slide rail is parallel with the length direction of the first slide rail, and the first slide rail and the second slide rail are positioned at two opposite sides of the inspection platform main body, and the first movable ruler is slidably jointed to the first slide rail and the second slide rail;
a length direction of fourth slide rail is parallel with the length direction of the third slide rail, and the third slide rail and the fourth slide rail are positioned at two opposite sides of the inspection platform main body, and the second movable ruler is slidably jointed to the third slide rail and the fourth slide rail.

8. The visual inspection apparatus for a glass substrate of a liquid crystal display according to claim 5, characterized in that the first pointer and the second pointer are laser pens.

9. An inspection method for a glass substrate of a liquid crystal display, characterized in that, the method comprising steps of:
locating the glass substrate for inspection fixedly on an inspection platform main body;
acquiring a corresponding coordinate via a coordinate reader installed on slide rails;
comparing the acquired coordinate with an inspection standard of the glass substrate to determine whether the glass substrate coincides the inspection standard;
wherein the slide rails are installed at two adjacent sides of the inspection platform main body leastwise, and length directions of the slide rails are parallel with a level of the inspection platform main body, and the lengths of the two adjacent slide rails are mutually perpendicular; the coordinate reader is slidably jointed to the slide rails,
wherein the step of acquiring the corresponding coordinate via the coordinate reader installed on the slide rails further comprises steps of:
controlling a first pointer sliding along a fifth slide rail;
controlling a second pointer sliding along a sixth slide rail;
acquiring the corresponding coordinate according to an optical line of the first pointer corresponding to the graduations of the first ruler and an optical line of the second pointer corresponding to the graduations of the second ruler;
wherein a length direction of the first ruler is parallel with a length direction of the fifth slide rail and corresponds to the first pointer; a length direction of the second ruler is parallel with a length direction of the sixth slide rail and corresponds to the second pointer.

10. The inspection method for a glass substrate of a liquid crystal display according to claim 9, characterized in that the step of acquiring a corresponding coordinate via the coordinate reader installed on the slide rails further comprises steps of:
controlling a first movable ruler sliding along a first slide rail;
controlling a second movable ruler sliding along a third slide rail;
acquiring the corresponding coordinate according to the first movable ruler and the second movable ruler;
wherein a length direction of the first movable ruler is perpendicular to a length direction of the first slide rail; a length direction of second movable ruler is perpendicular to a length direction of the third slide rail.

11. The inspection method for a glass substrate of a liquid crystal display according to claim 10, characterized in that the step of acquiring a corresponding coordinate via the coordinate reader installed on the slide rails further comprises steps of:
controlling the first movable ruler sliding along the first slide rail and a second slide rail;
controlling the second movable ruler sliding along the third slide rail and a fourth slide rail;
acquiring the corresponding coordinate according to the first movable ruler and the second movable ruler;
wherein a length direction of second slide rail is parallel with the length direction of the first slide rail, and the first slide rail and the second slide rail are positioned at two opposite sides of the inspection platform main body; a length direction of fourth slide rail is parallel with the length direction of the third slide rail, and the third slide rail and the fourth slide rail are positioned at two opposite sides of the inspection platform main body.

12. The inspection method for a glass substrate of a liquid crystal display according to claim 9, characterized in that the first pointer and the second pointer are laser pens.

* * * * *